(12) United States Patent
Swayze et al.

(10) Patent No.: US 6,932,517 B2
(45) Date of Patent: Aug. 23, 2005

(54) CONNECTOR INCORPORATING A CONTACT PAD SURFACE ON A PLANE PARALLEL TO A LONGITUDINAL AXIS

(75) Inventors: Jeffrey S. Swayze, Hamilton, OH (US); Benjamin F. James, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 229 days.

(21) Appl. No.: 09/967,046

(22) Filed: Sep. 28, 2001

(65) Prior Publication Data

US 2002/0081871 A1 Jun. 27, 2002

Related U.S. Application Data

(60) Provisional application No. 60/243,669, filed on Oct. 27, 2000.

(51) Int. Cl.[7] .................................................. G02B 6/42
(52) U.S. Cl. ............................ 385/88; 385/62; 385/75
(58) Field of Search ............................ 385/62, 65, 75, 385/88; 600/345

(56) References Cited

U.S. PATENT DOCUMENTS

| | | | |
|---|---|---|---|
| 4,297,569 A | 10/1981 | Flies | |
| 4,326,125 A | 4/1982 | Flies | |
| 4,379,966 A | 4/1983 | Flies | |
| 4,436,993 A | 3/1984 | Flies | |
| 4,578,573 A | 3/1986 | Flies et al. | |
| 4,752,679 A | 6/1988 | Wehrmacher | |
| 4,795,647 A | 1/1989 | Leibfred | |
| 4,822,997 A | * 4/1989 | Fuller et al. | 356/73.1 |
| 4,897,789 A | 1/1990 | King et al. | |
| 4,898,446 A | * 2/1990 | Hinckley | 385/72 |
| 5,029,973 A | 7/1991 | Rink | |
| 5,074,637 A | 12/1991 | Rink | |
| 5,214,732 A | 5/1993 | Beard et al. | |
| 5,246,422 A | 9/1993 | Favre | |
| 5,351,268 A | 9/1994 | Jensen et al. | |
| 5,419,717 A | 5/1995 | Abendschein et al. | |
| 5,428,703 A | 6/1995 | Lee | |
| 5,454,807 A | 10/1995 | Lennox et al. | |
| 5,515,466 A | 5/1996 | Lee | |
| 5,643,212 A | 7/1997 | Coutre et al. | |
| 5,742,718 A | 4/1998 | Harman et al. | |
| 5,802,229 A | 9/1998 | Evans et al. | |
| 6,068,627 A | 5/2000 | Orszulak et al. | |
| 6,250,818 B1 | 6/2001 | Loughlin et al. | |

FOREIGN PATENT DOCUMENTS

| | | |
|---|---|---|
| EP | 0 296 467 A2 | 12/1988 |
| EP | 0951921 A2 | 10/1999 |
| WO | WO 99/67156 A | 12/1999 |

OTHER PUBLICATIONS

EPO Search Report dated Oct. 21, 2004 for corresponding patent application, European Patent Application No. EP 01 98 8873.

* cited by examiner

*Primary Examiner*—John D. Lee
*Assistant Examiner*—Eric Wong

(57) ABSTRACT

An improved connector capable of transferring both energy and electrical signals between an energy generator and an energy transfer device is disclosed. The connector attaches the energy transfer device to the energy generator by rotation about a longitudinal axis. The connector carries at least one contact pad that has a surface on a plane parallel to the longitudinal axis. A line passing through the surface of the contact pad perpendicular to the plane is skew to the longitudinal axis, so that rotation of the connector engages the contact pad with conductive contacts associated with the energy generator in a direction substantially perpendicular to the contact pad.

19 Claims, 12 Drawing Sheets

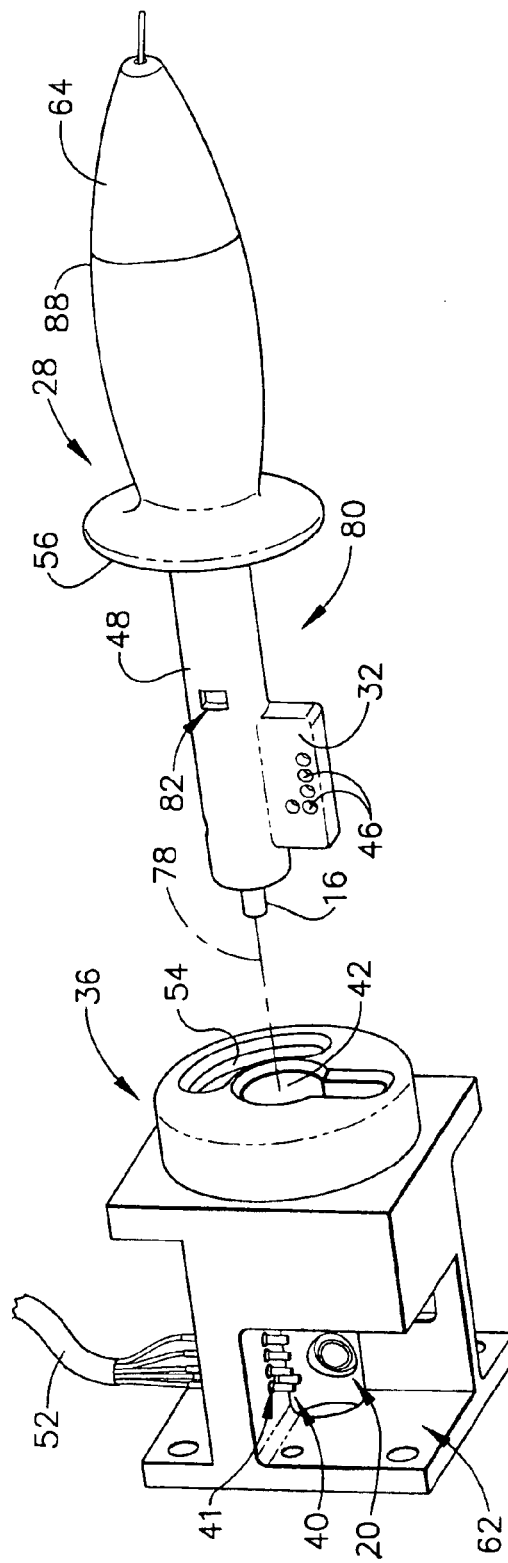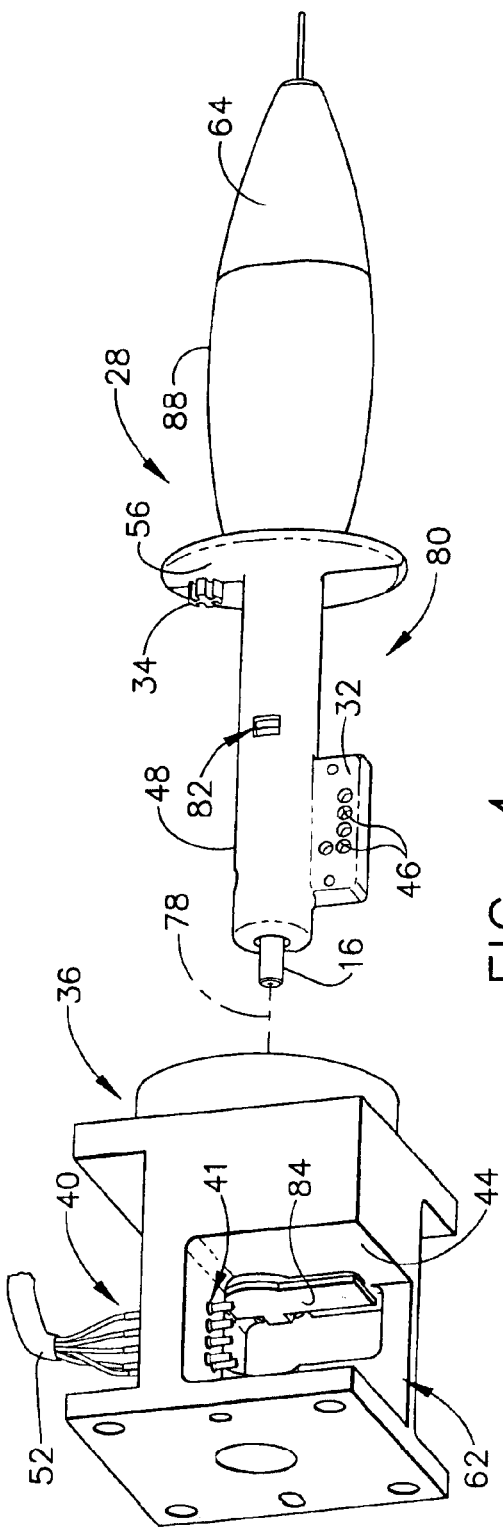
FIG. 3
FIG. 4

CONNECTOR INCORPORATING A CONTACT PAD SURFACE ON A PLANE PARALLEL TO A LONGITUDINAL AXIS

This application claims the benefit of U.S. Provisional Application No. 60/243,669, filed Oct. 27, 2000.

FIELD OF THE INVENTION

The present invention relates, in general, to an improved connector to transfer energy from an energy generator and an energy transfer device and electrical signals between at least one conductive contact on the energy generator and at least one contact pad on the energy delivery device, and more particularly, to an improved connector rotatably attachable to an energy generator wherein the rotation of the connector about a longitudinal axis engages the electrical contact pad with the conductive contact in a direction substantially perpendicular to the contact surface of the contact pad.

BACKGROUND OF THE INVENTION

Systems to transfer energy to tissue have been used in the medical field for therapeutic treatment of tissue. These systems generally comprise an energy generator and an energy delivery device. The energy delivery device attaches to the energy generator with a connector. The energy generator can be a reusable piece of capital equipment such as a laser, ultrasonic generator, or radio-frequency electrical generator. The energy delivery device is usually inexpensive relative to the energy generator and has a limited design life relative to the life of the energy generator.

Some energy generators carry computers to monitor the usage of the generators. It can be advantageous for energy delivery devices associated with computerized energy generators to carry a memory device to record information about the usage of the energy delivery device. This information can be, for example, the amount of energy transmitted, the number of uses of the energy delivery device, and any errors generated during the use of the energy delivery device. When the energy delivery device is used again, the computer can access the memory device within the energy delivery device and can use the information recorded in the memory to make decisions regarding the energy delivery device.

When utilizing an energy delivery device that exchanges information with an energy generator, electrical communication between the energy generator and the energy delivery device must be established to transfer electrical signals between the computer and the energy delivery device. The connector on the energy delivery device must transfer energy from the generator and exchange information with the memory associated with the energy delivery device. Such a connector may be used to exchange both energy and electrical signals with the energy generator. Electrical contacts may be used to exchange electrical signals, and other contacts, such as optical fiber connectors, may be used to exchange energy supplied by the energy generator.

Locating the necessary electrical signal contacts within one connector presents problems for a designer of the connector. Surface area must be found on or within both the generator and the connector to accommodate the transfer of both electrical signals and treatment energy. Tolerances must be considered when locating such electrical signal contacts and energy transfer attachments within the same connector. Contacts must be shielded from adverse environmental conditions, such as, for example, spills and moisture. As the energy generator can be a reusable piece of capital equipment, the electrical contacts on the energy generator must be designed for a long useful life. The connector must attach securely to the energy generator so that it does not become inadvertently detached. The connector should have a positive tactile feel to notify a user of a good connection when the user attaches it.

Prior art connectors that transfer energy through to an energy delivery device while also carrying electrical contacts have used various designs to accommodate design needs. Abendschein et al, in U.S. Pat. No. 5,419,717, illustrates a connector that has an electrical portion and an optical portion. Both electrical portion and optical portion connect with a linear push of the connector. The connector of Abendschein carries electrical contacts on a circuit board, and the circuit board is mounted with clearances to self-align with an electrical receptor. The self-alignment compensates for positional tolerances in manufacture. Harman et al, in U.S. Pat. No. 5,742,718, discusses a threaded optical fiber connector having a tethered data module component. The threaded optical fiber connector screws onto a laser source, and the data module component inserts into a separate slot on the laser source.

Prior art connectors for energy-transfer systems have not adequately fulfilled users' needs. Connectors that attach with a straight push and no rotation may give unsatisfactory tactile feedback to the user of an adequate connection. Connectors attaching with rotation and having a separate tethered part for an electrical computer connection require handling the second tethered part to link the electrical connection. Connectors attaching with rotation to energy generators may have electrical contacts that use sliding contact when the connector is rotated, limiting design life of the contacts on the energy generator through friction and wear. What is needed, therefore, is a connector that delivers energy and electrical signals in one body attachable to an energy generator with a rotational movement, and has electrical contacts that engage the energy generator without substantial sliding. What is needed is a connector that has electrical contacts positioned so that rotation of the connector engages contact pads on the connector to the conductive contacts of the energy generator in a direction substantially perpendicular to the contact surfaces of the contact pads. What is further needed is a connector with contact pads positioned on a plane of a flange radially extending from the longitudinal axis of rotation of the connector. What is further needed is for a memory device also to be contained with the contact pads on a printed circuit board within the flange, so that the memory device and the electrical contacts are contained in a single, unitary piece that can be economically molded.

SUMMARY OF THE INVENTION

An improved connector for attaching a usage-limited delivery device to an energy generator comprises at least one electrical contact pad having a contact surface located on a plane parallel to the axis of rotation of the connector and positioned so that rotation of the connector engages the contact pad to a conductive contact on the energy generator in a direction substantially perpendicular to the contact pad. An embodiment of the connector places several contact pads within a flange radially extending from the longitudinal axis of the connector. The flange can also have an associated memory device and can contain the memory device and contact pads as a printed circuit board assembly insert-molded into the flange. The connector is rotatable from an unlocked position having the contact pads disengaged from the conductive contacts to a locked position having the contact pads engaged with the conductive contacts. When the connector is rotated into the locked position, a wall on a connector housing obstructs proximal movement of the flange on the connector to prevent removal of the connector from the housing.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is an isometric view of the connector and connector housing shown in FIG. 1.

FIG. 4 is an isometric view from a second angle of the connector and connector housing of FIG. 3.

DETAILED DESCRIPTION OF THE INVENTION

Figure 1:
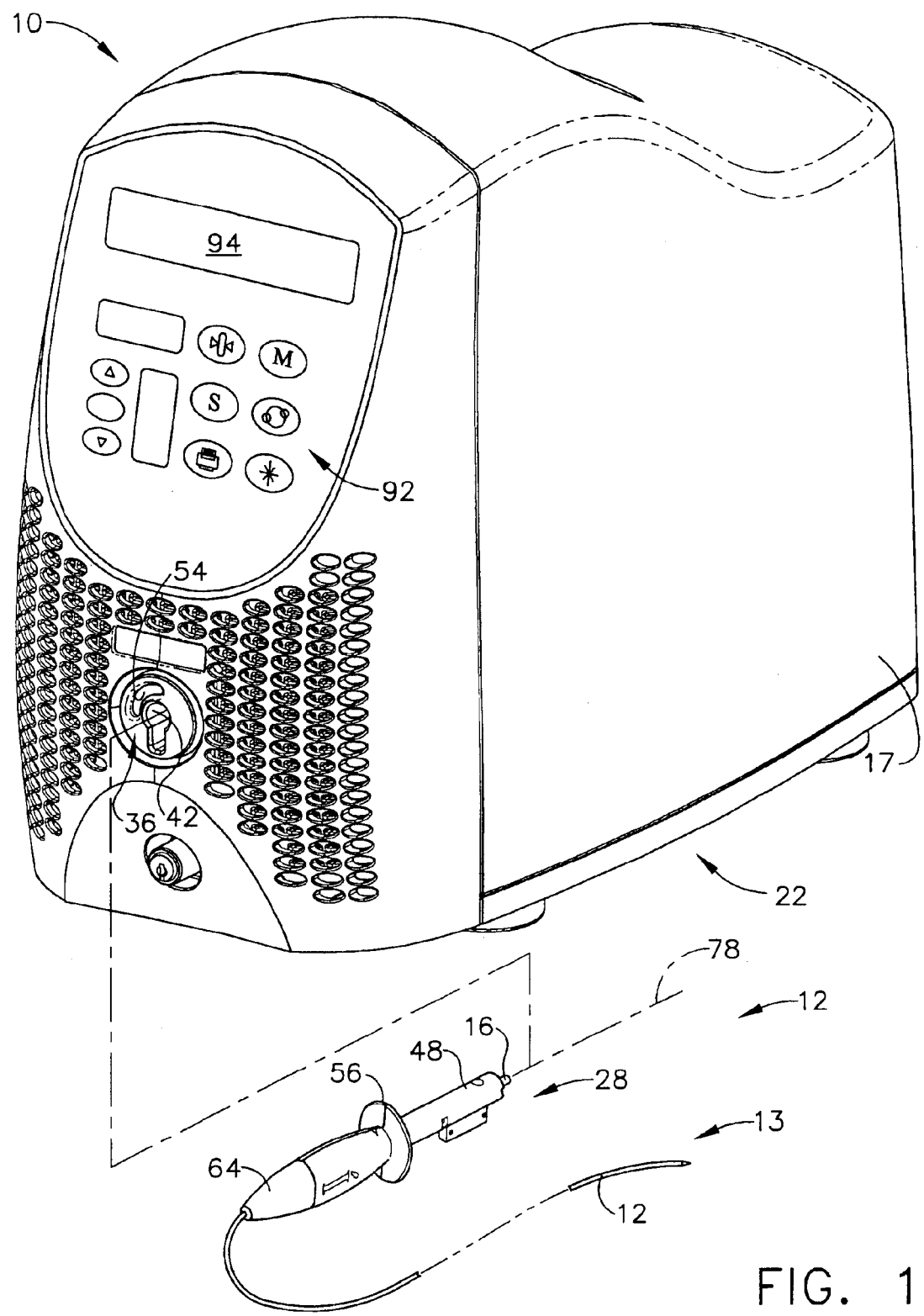
FIG. 1 is an isometric view of a system for transferring diffuse light to tissue, including a laser and an optical fiber assembly, incorporating a connector and connector housing according to an embodiment of the present invention.

FIG. 1 shows a system 10 for transferring diffused light to human tissue incorporating a connector according to an embodiment of the present invention. A laser 22 is provided with system 10 to generate energy in the form of laser light. A cover 17 shields interior components of laser 22, and a connector housing 36 resides within a front portion of cover 17. The front of connector housing 36 is exposed to the exterior. System 10 further includes an optical fiber assembly 12 having connector 28 at its proximal end. Optical fiber assembly 12 is attachable to connector housing 36 by inserting connector 28 through an opening 42 in connector housing 36. An optical fiber 13 extends proximally from connector 28. Optical fiber 13 may be, for example, a standard optical fiber possessing a light transmitting core, cladding, and a jacket. Optical fiber 13 may have a diffuser tip located at the end opposite connector 28. The diffuser tip may be used to diffuse light for medical treatment of tissue.

Figure 2:
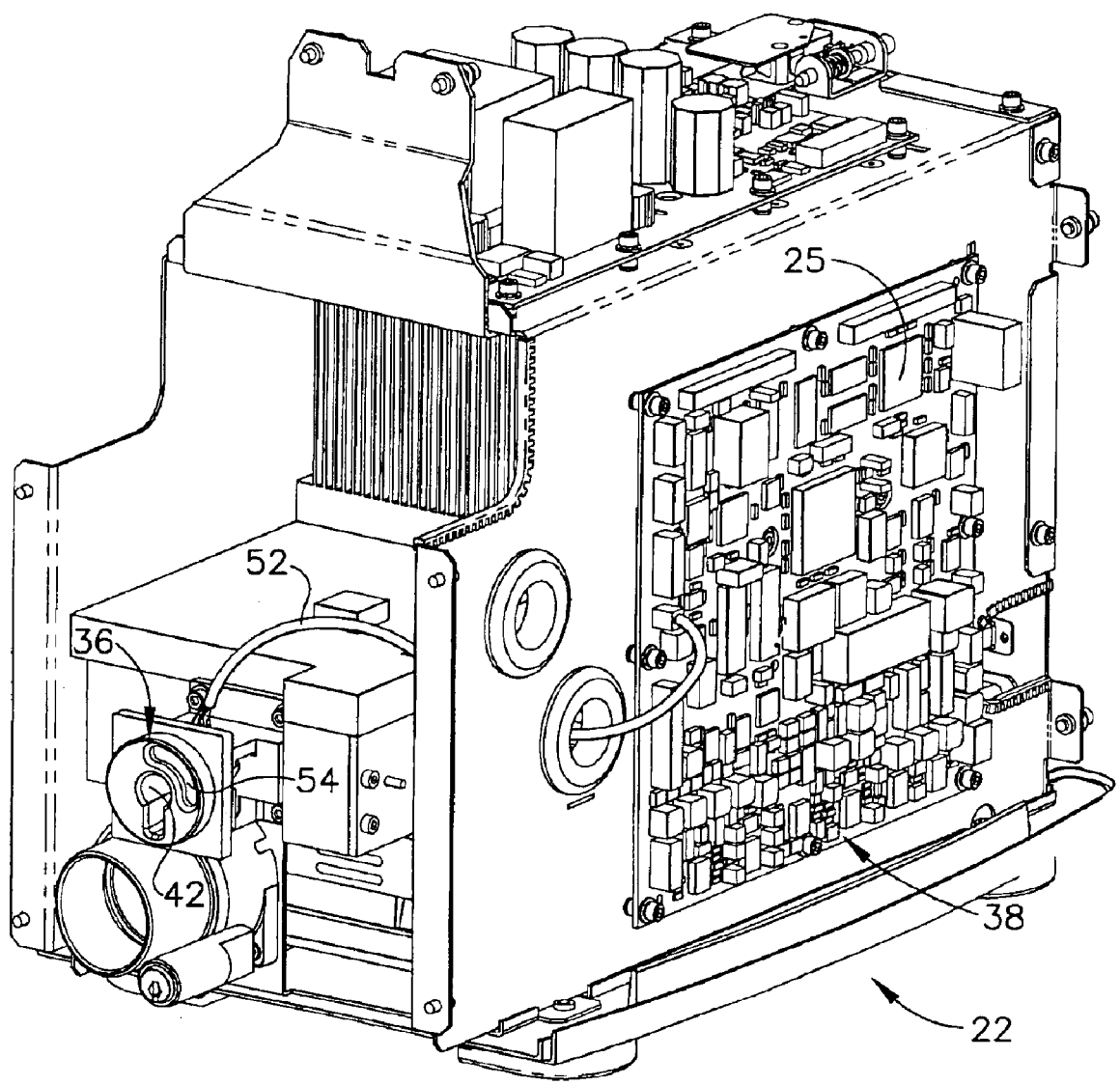
FIG. 2 is an isometric view of the laser in FIG. 1 with the cover removed, exposing interior elements of the laser.

FIG. 2 depicts laser 22 with cover 17 removed to expose interior portions of laser 22. Conductor cable 52 electrically joins connector housing 36 to controller board 38 on laser 22. Located on controller board 38 is a computer in the form of main processor 25, which receives and processes electronic signals to control the operation of system 10. Main processor 25 can be, for example, a microprocessor. Signals from electronic components within optical fiber assembly 12 (FIG. 1) communicate via conductor cable 52 with controller board 38 and main processor 25.

FIG. 3 depicts connector 28 and connector housing 36. Connector 28 inserts into connector housing 36 and locks into connector housing 36 by rotation about a longitudinal axis 78. Connector 28 possesses a handle portion 88, shaped for easy grasping by the user, and capped on the proximal end with a boot 64. A barrel 48 continues distally from handle portion 88. A connector face 56 separates barrel 48 from handle portion 88. Attached to barrel 48 is a flange 32 radially extending from longitudinal axis 78. Flange 32 includes contact pad access openings 46 placed on a large side of flange 32. An axial gap 80 separates the proximal end of flange 32 from connector face 56. The distal end of a ferrule 16 protrudes from the distal end of barrel 48. Ferrule 16 is one form of an energy transfer attachment for transferring energy from laser 22 to optical fiber assembly 12 for medical treatment. Ferrule 16 is located within connector 28 distal of handle portion 88.

FIG. 3 further shows that connector housing 36 has an opening 42 on its proximal face, allowing entrance of connector 28 into connector housing 36. Opening 42 is shaped to accommodate barrel 48 and flange 32 as they enter connector housing 36. Slot 54, describing an arcuate path, also is situated on the proximal face of connector housing 36. Within the interior of connector housing 36 is flange area 62 providing enough clearance for rotation of flange 32 within connector housing 36. Also provided on connector housing 36 is at least one, and preferably a set of, spring-loaded pins 40. Spring-loaded pins 40 are designed to press against electrical contact pads of a printed circuit board to make excellent electrical contact. Spring-loaded pins 40 mount to connector housing 36 using receptacles 41. Suitable spring-loaded pins 40 are available from Interconnect Devices, Inc. in Kansas City, Kans., as part number R-SS-100-CR. Suitable receptacles 41, also available from Interconnect Devices, Inc. in Kansas City, Kans., have the part number SS-19-3.8-G. Connecting to and in electrical communication with spring-loaded pins 40 is conductor cable 52. Detent 20 is also provided within the interior of connector housing 36, providing tactile feedback and retention as will be further described. A suitable detent 20 can be purchased from Vlier in Brighton, Mass., as part number 62123385.

FIG. 4 illustrates connector 28 and connector housing 36 from a second angle to display additional features. Connector 28 also provides an anti-torque feature 34 placed on connector face 56. Anti-torque feature 34 engages slot 54 (FIG. 3) when connector 28 is placed into connector housing 36. A wall 44 on connector housing 36 becomes more visible on FIG. 4. Wall 44 lies proximal to flange 32 when connector 28 is fully inserted through opening 42 into connector housing 36. Connector housing 36 further comprises shutter 84, covering the distal end of opening 42 into wall 44. Shutter 84 is shown spring-loaded into the position covering opening 42, and can rotate when contacted by connector 28 to permit the entrance of connector 28 into connector housing 36.

Figure 5:
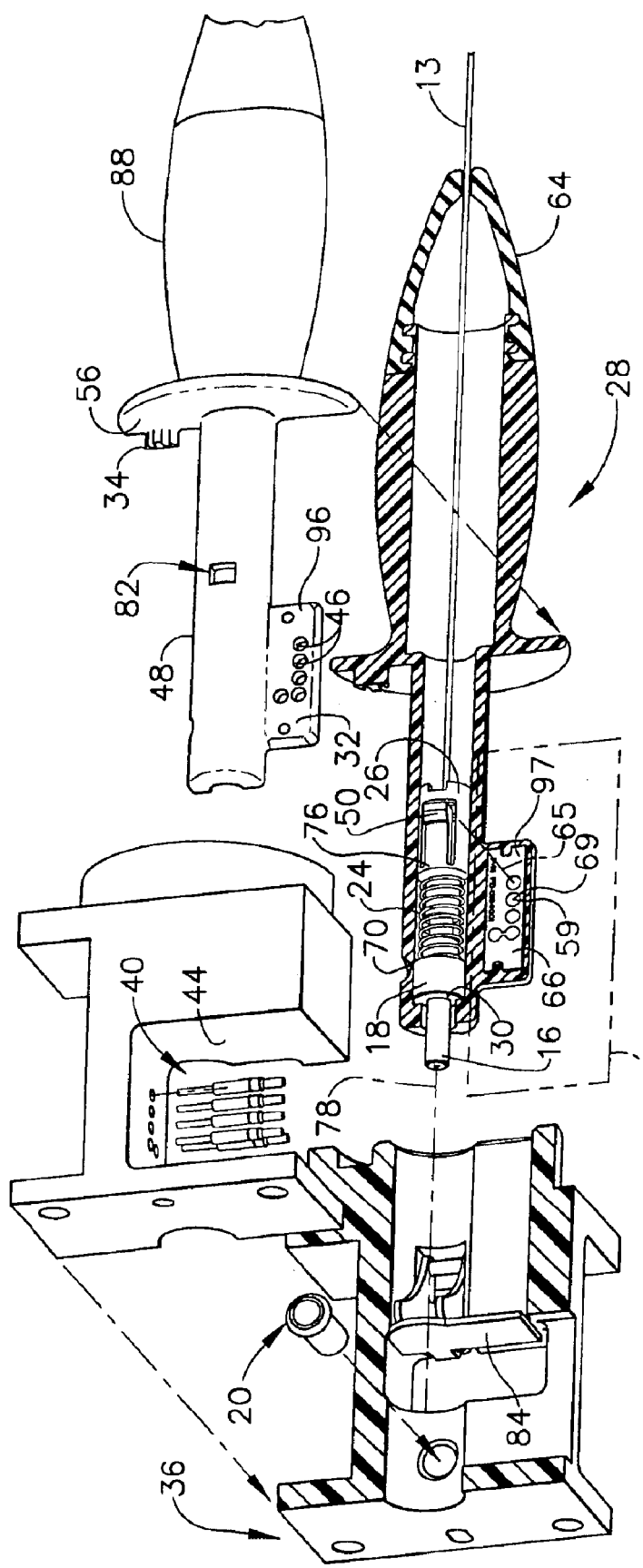
FIG. 5 is an exploded isometric view of the connector and connector housing of FIG. 3.

FIG. 5 is an exploded isometric depicting the interior portions of connector housing 36 and connector 28. Detent 20 can be seen to insert into a retention hole near the distal end of connector housing 36. The retention hole is created substantially perpendicular to the access way for barrel 48. Also on connector housing 36, shutter 84 is shown to include an arcuate cam surface which contacts the distal edge of barrel 48 as connector 28 moves distally within connector housing 36. Spring-loaded pins 40 are seen in position to assemble into housing 36. Ferrule 16 resides near the distal end of connector 28. Ferrule 16 has a distal opening to admit light energy generated by laser 22 (FIG. 1) into optical fiber 13. An enlarged diameter portion 18 sized only slightly smaller than the inner diameter of barrel 48 is located on ferrule 16. Enlarged diameter portion 18 of ferrule 16 fits into inner diameter of barrel 48 with a slip fit and has axial freedom of movement. The proximal portion of ferrule 16 has a smaller diameter sized to fit within the inner diameter of a spring 24 to radially locate the distal end of spring 24. The distal end of spring 24 exerts force against enlarged diameter portion 18 of ferrule 16 to urge ferrule 16 axially against seating surface 30. Retainer 26 restrains the proximal end of spring 24 and compresses spring 24 to generate the bias force urging ferrule 16 distally relative to connector 28. The distal end of retainer 26 has a second, smaller diameter to radially locate the proximal end of spring 24. Retainer 26 carries at least one locking feature 50. Locking feature 50 on retainer 26 can be a cantilever beam with a protruding snap fit hook. The snap fit hook protrudes into snap fit retention feature 82. Locking feature 50 latching into snap fit retention feature 82 prevents axial movement of retainer 26 under the reactive force of spring 24.

FIG. 5 shows that the interior of handle portion 88 is larger than enlarged portion 18 of ferrule 16 and enlarged portion 76 of retainer 26. The enlarged interior of handle portion 88 facilitates assembly of ferrule 16 and retainer 26 into connector 28 from the open proximal end of handle portion 88. Boot 64 protects the interior parts from adverse environmental conditions. Boot 64 can be made from a flexible material, for example, rubber, and can fit over ridges on the proximal end of handle portion 88 to stay in position. Boot 64 surrounds and retains optical fiber 13 as it emerges from handle portion 88 of connector 28.

FIG. 5 further displays printed circuit board 66 within flange 32. Printed circuit board 66 includes two large flat surfaces and a plurality of surrounding edges of relatively smaller surface area. At least one, and preferably several, electrically conductive contact pads 59, each having a contact surface 69, are situated on a large flat surface of printed circuit board 66, shown as mating surface 97. Mating surface 97 is situated within flange 32 to define a contact pad plane 61 parallel to longitudinal axis 78. Contact pad plane 61 is defined on connector 28, and each contact surface 69 of each contact pad 59 lies on contact pad plane 61. A contact pad perpendicular line 65 can be shown perpendicular to each contact surface 69 of each contact pad 59. Contact pad perpendicular line 65 does not intersect longitudinal axis 78, and is thus skew to longitudinal axis 78.

Printed circuit board 66 can be insert-molded into flange 32 leaving only contact pads 59 open to the exterior through access openings 46. Insert molding printed circuit board 66 into connector 28 can substantially enclose printed circuit board 66 and associated contact pads 59 protecting printed circuit board 66 from environmental elements such as moisture, dust, body fluids, or chemicals. Connector 28 can be molded of non-conductive material such as plastic. The non-conductive material surrounds contact pads 59 on all sides in directions parallel to mating surface 97. Contact pads 59 are accessible in a direction substantially perpendicular to mating surface 97 through pad access openings 46.

Figure 6:
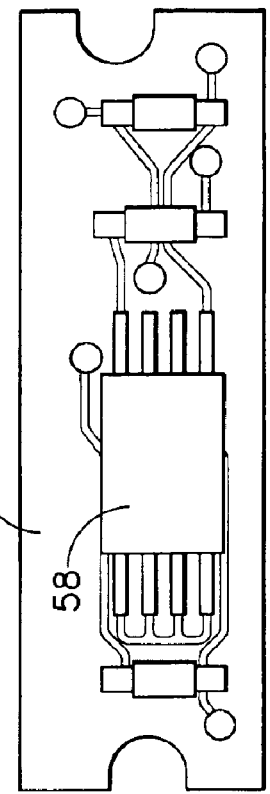
FIG. 6 is a plan view showing a memory device on the printed circuit board incorporated into the connector of FIG. 3.

FIG. 6 depicts the side opposite mating side 97 on printed circuit board 66. A memory device 58 resides on the side of printed circuit board 66 opposite mating side 97 and is in electrical communication with contact pads 59. Memory device 58 can be, for example, an electronic erasable programmable read-only memory device (EEPROM) and can store information useful to the operation of system 10 (FIG. 1).

Figure 7:
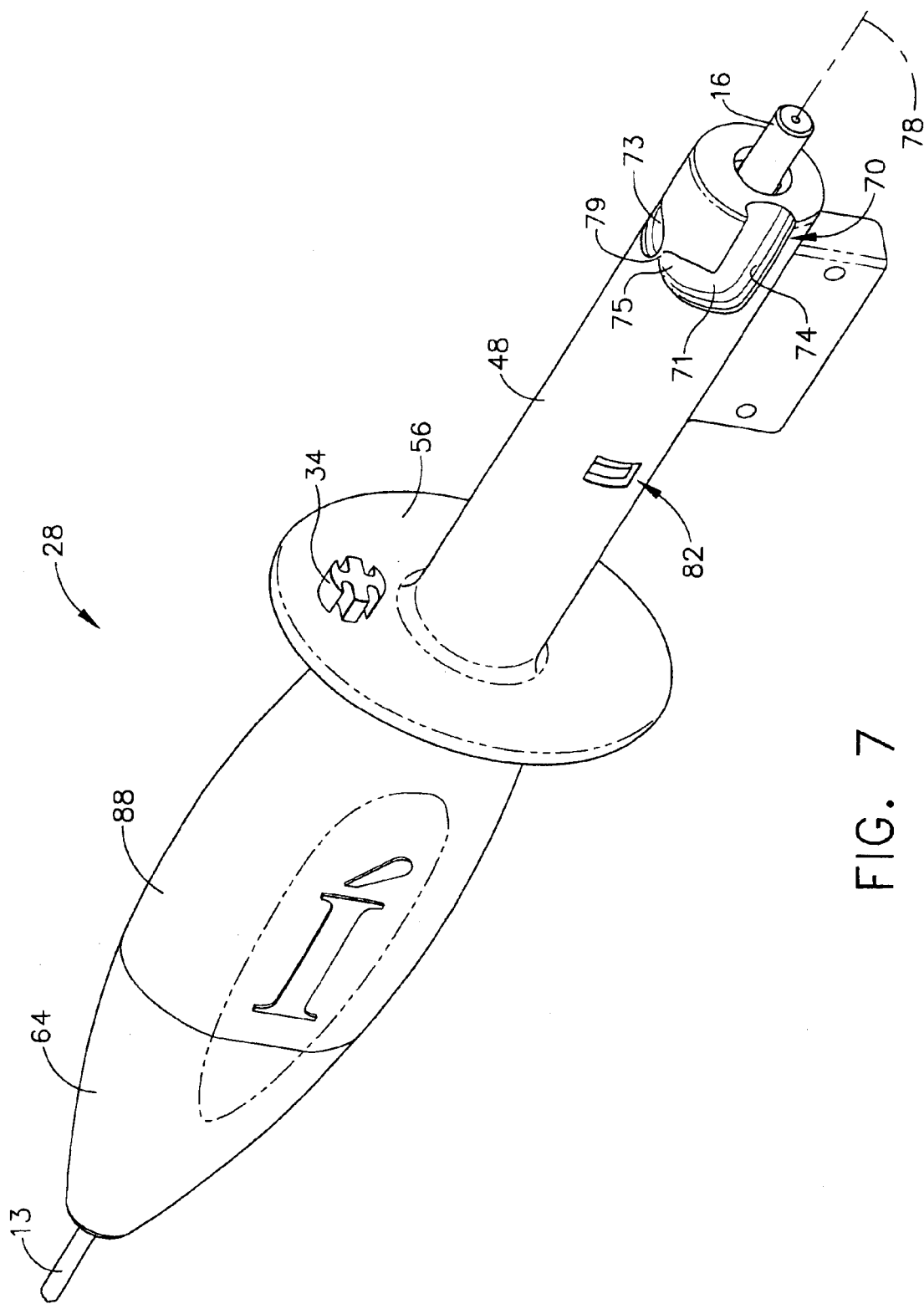
FIG. 7 is another isometric view of the connector of FIG. 1 showing a detent groove.

FIG. 7 shows connector 28 from another angle for better viewing of detent groove 70, located on the surface of barrel 48. As can be seen, detent groove 70 has an axial groove portion 74 and a circumferential groove portion 75 intersecting at a detent angle 71. Detent groove 70 is fashioned to engage detent 20 when connector 28 is inserted deeply into connector housing 36. The depth of detent groove 70 varies with position along detent groove 70, inducing detent 20 to apply varying position-dependant force levels to connector 28. The circumferential groove portion 75 is as deep as axial groove portion 74 where they intersect at detent angle 71. Circumferential groove portion 75 becomes increasingly shallow as it wraps around connector 28 until circumferential groove portion 75 reaches the shallowest portion 79. Circumferential groove portion 75 then becomes abruptly deeper again at detent contact point 73.

Figure 8:
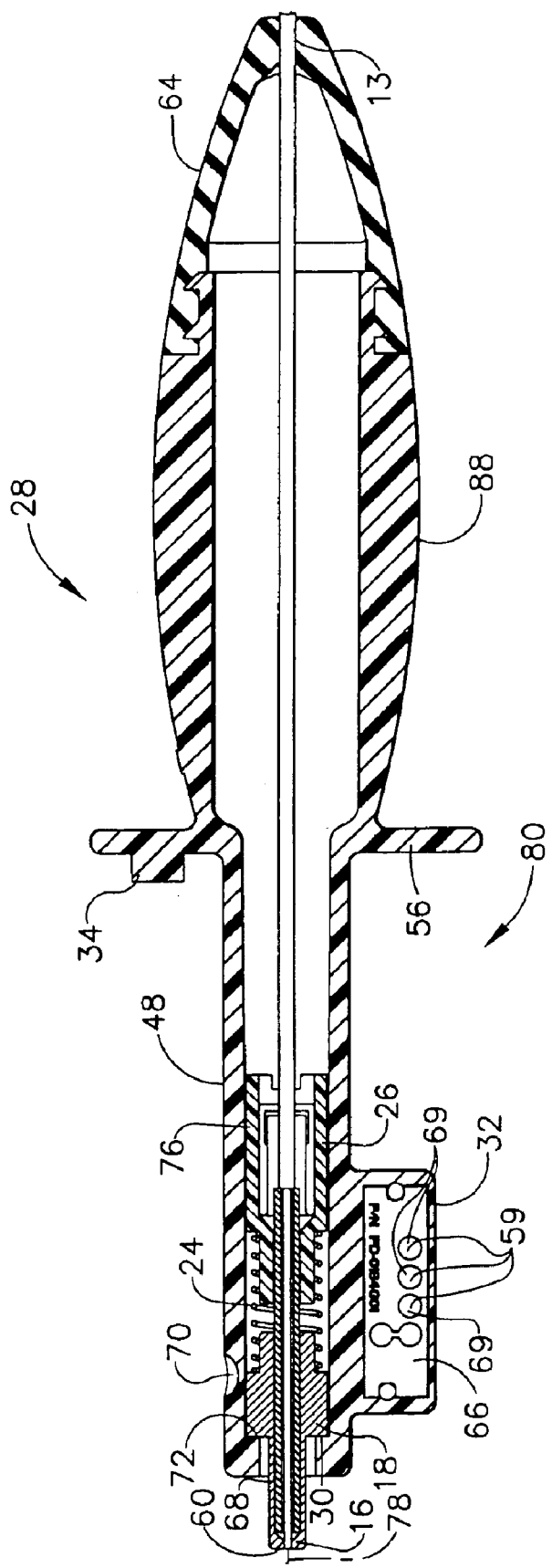
FIG. 8 is a section view taken in side elevation along the centerline of the connector shown in FIG. 1.

FIG. 8 shows a section view of connector 28. Interior parts of connector 28 are also shown in section view. Bushing 68 lies inside the inner diameters of ferrule 16 and retainer 26. The outer layer of bushing 68 is bonded into the inner diameter of ferrule 16, while the outer layer of bushing 68 can slip through the inner diameter of retainer 26. Epo-Tek 302-3M epoxy, available from Epoxy Technology in Billerica, Mass., can be used to bond bushing 68 to inner diameter of ferrule 16. Bushing 68 is made of a material such as polycarbonate that can bond easily to ferrule 16.

A portion of optical fiber 13 is located inside the inner diameter of bushing 68. Optical fiber 13 is stripped of jacket and cladding for most of its length within bushing 68, however, the jacket and cladding extend into the proximal end of bushing 68 for a short distance. The short extension of jacket and cladding into the proximal end of bushing 68 serves as stress relief for optical fiber 13.

Optical fiber 13 is bonded to the interior of bushing 68. The same adhesive used to bond bushing 68 to inner diameter of ferrule 16 can be used to bond the bare optical fiber core of optical fiber 13 to bushing 68. The material of bushing 68 facilitates bonding, as the jacket of optical fiber 13 may be created from a material containing perfluoroalkoxy that does not bond easily.

Figure 9:
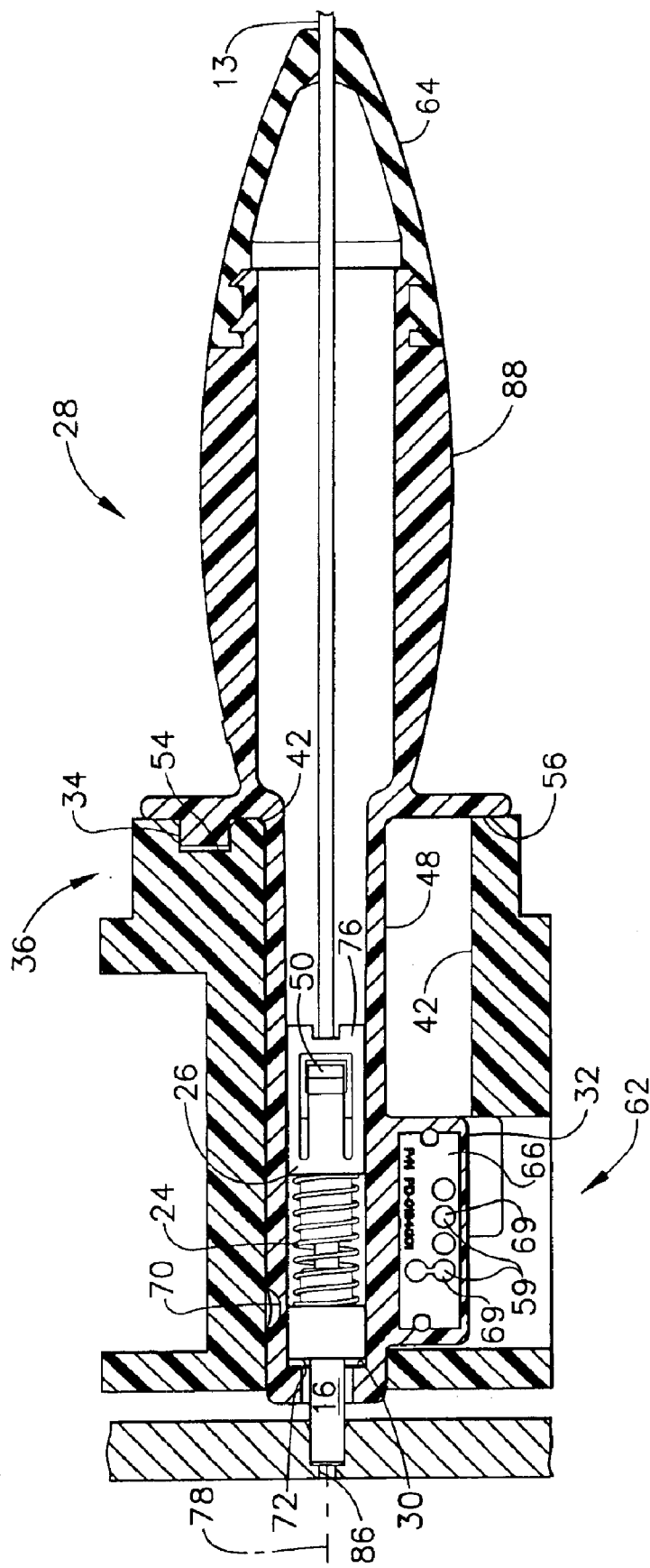
FIG. 9 is a section view taken in side elevation along the centerline of the connector and connector housing shown in FIG. 10.

FIG. 9 depicts connector 28 inserted into connector housing 36 in the unlocked position. Connector 28 is assembled to connector housing 36 by grasping connector 28 at handle portion 88 and inserting connector 28 into opening 42 of connector housing 36. Barrel 48 and flange 32 of connector 28 pass through opening 42 upon insertion. Connector 28 contacts and rotates shutter 84 (FIG. 5) into a position to allow radiant energy to pass through optical fiber 13. When connector 28 is far within connector housing 36 the ball end of detent 20 (FIG. 5) engages detent groove 70. Detent 20 then rides within detent groove 70 along the axial groove portion 74 of detent groove 70. Because detent 20 is located distant from opening 42, detent 20 does not engage connector 28 until connector 28 is well within connector housing 36. A user will feel tactile feedback from the force of detent 20 engaging detent groove 70, signifying the deep insertion of connector 28 into connector housing 36.

FIG. 9 further illustrates ferrule 16 engaging an energy exit port 86 on connector housing 36 when connector 28 moves into connector housing 36. The ability of ferrule 16 to move axially relative to connector 28 compensates for manufacturing tolerances so that ferrule 16 is always forced against energy exit port 86. Axial movement of connector 28 after engaging the end of ferrule 16 with energy exit port 86 causes spring 24 to compress. Shoulder 72 of ferrule 16 lifts off of seating surface 30 of connector 28. Ferrule 16 slips through connector 28 carrying optical fiber 13, as optical fiber 13, bonded to bushing 68, moves proximally through the inner diameter of retainer 26. Spring 24 transfers force through retainer 26 to locking features 50. The end of spring 24 that is against enlarged portion 76 of retainer 26 does not move. The user continues to insert connector 28 until connector face 56 makes contact with the proximal side of connector housing 36. When connector face 56 makes contact with the proximal side of connector housing 36 the user feels a high resistance force and cannot push connector 28 any further.

Figure 10:
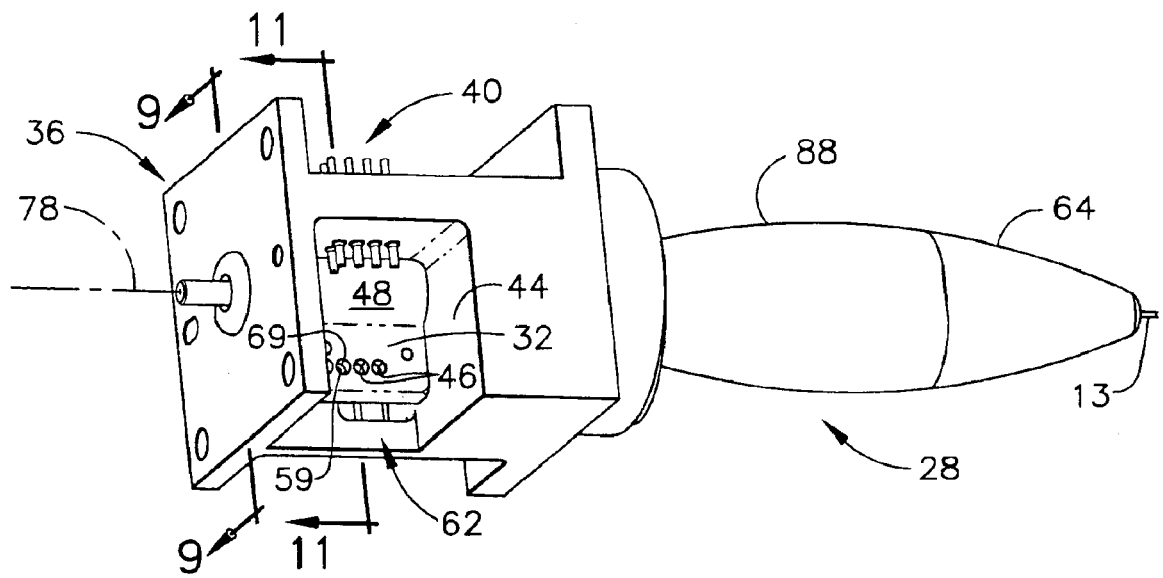
FIG. 10 is an isometric view of the connector of FIG. 1 inserted into the housing of FIG. 1 in the unlocked position.
Figure 11:
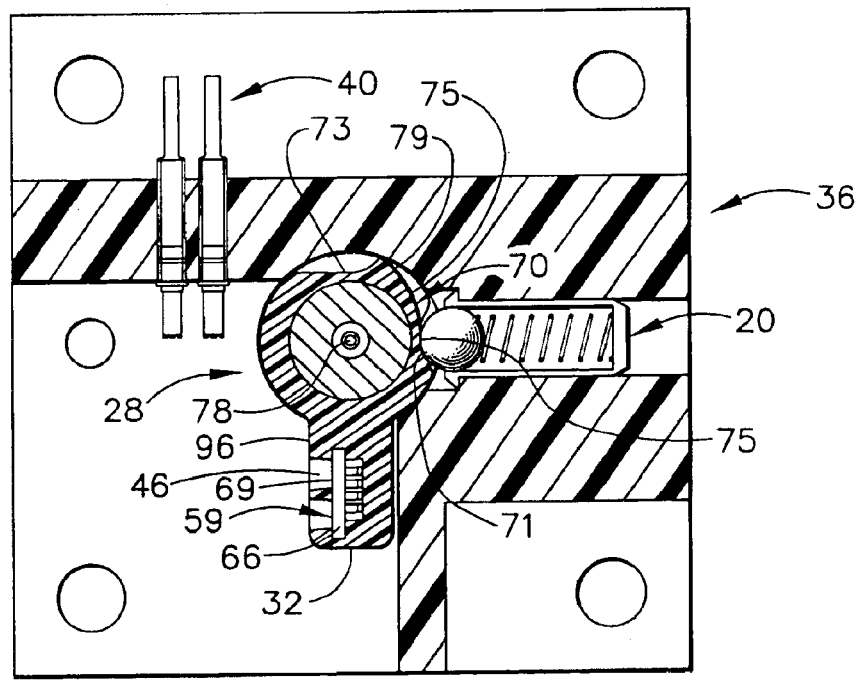
FIG. 11 is a section view taken generally along line 11—11 of FIG. 10.

FIG. 10 and FIG. 11 illustrate other views of connector 28 inserted into connector housing 36 in the unlocked position. FIG. 10 depicts contact pads 59, in this unlocked position, are not engaged with spring-loaded pins 40. FIG. 11 illustrates that the ball of detent 20 engages detent groove 70 at detent angle 71 of detent groove 70. Connector 28 must be rotated about longitudinal axis 78 to the locked position to complete the assembly.

Figure 12:
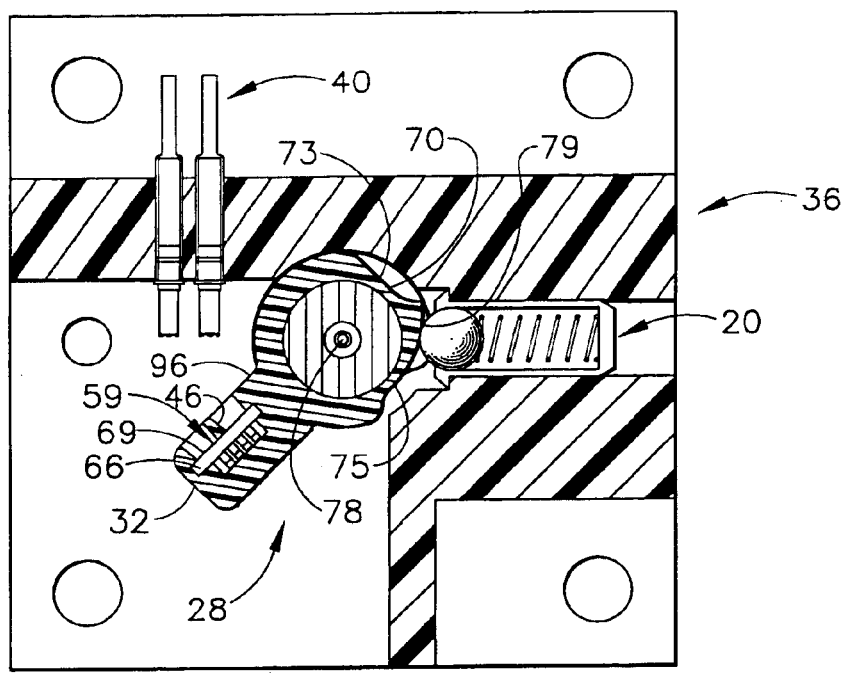
FIG. 12 is the view of FIG. 11 with the connector rotated 45 degrees clockwise with respect to the housing.

FIG. 12 shows a section view of connector 28 rotated to an intermediate position between locked and unlocked. As connector 28 rotates, the ball end of detent 20 follows the circumferential portion 75 of detent groove 70. Detent 20 first encounters a shallower portion of detent groove 70 and then a deeper portion. The shallow portion of detent groove 70 depresses the ball of detent 20 further against spring 20 to generate more force from detent 20. The user senses the increased force as an increase in torque required to rotate connector 28 until detent 20 engages shallowest groove portion 79. At that point, an abrupt deepening of detent groove 70 to detent point 73 causes detent 20 to suddenly decrease the force exerted against detent groove 70. The decrease in force is sensed by the user as a decrease in torque, and the decrease in torque signals the user that connector 28 is nearing the locked position. In the locked position, detent 20 is in a locally deepest portion of detent groove 70, at detent contact point 73, so that the locked position is a stable position.

Figure 13:
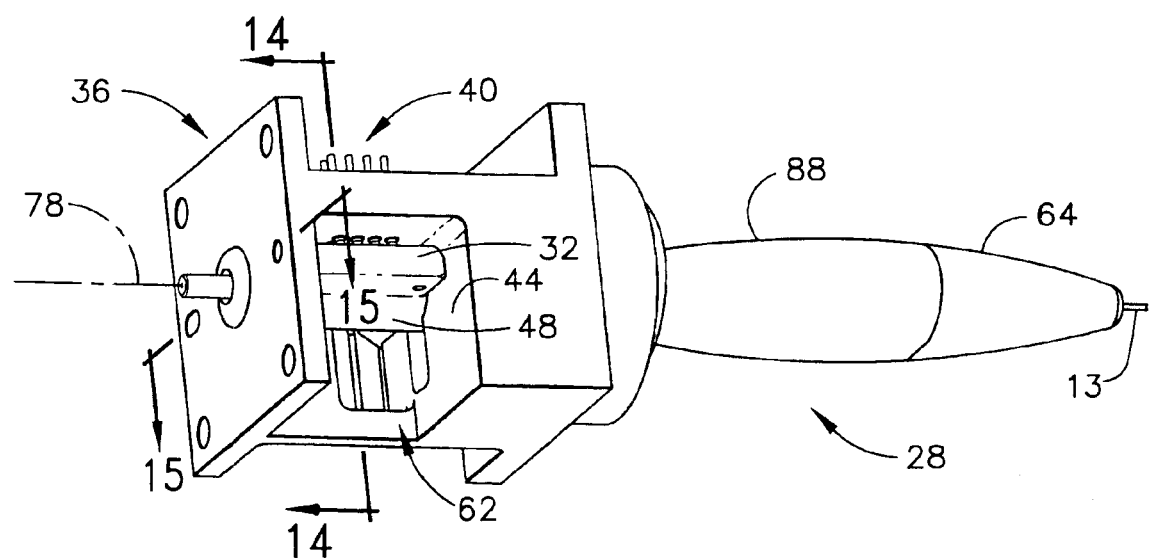
FIG. 13 is an isometric view of the connector of FIG. 1 inserted into the connector housing of FIG. 1 and rotated to the locked position.
Figure 14:
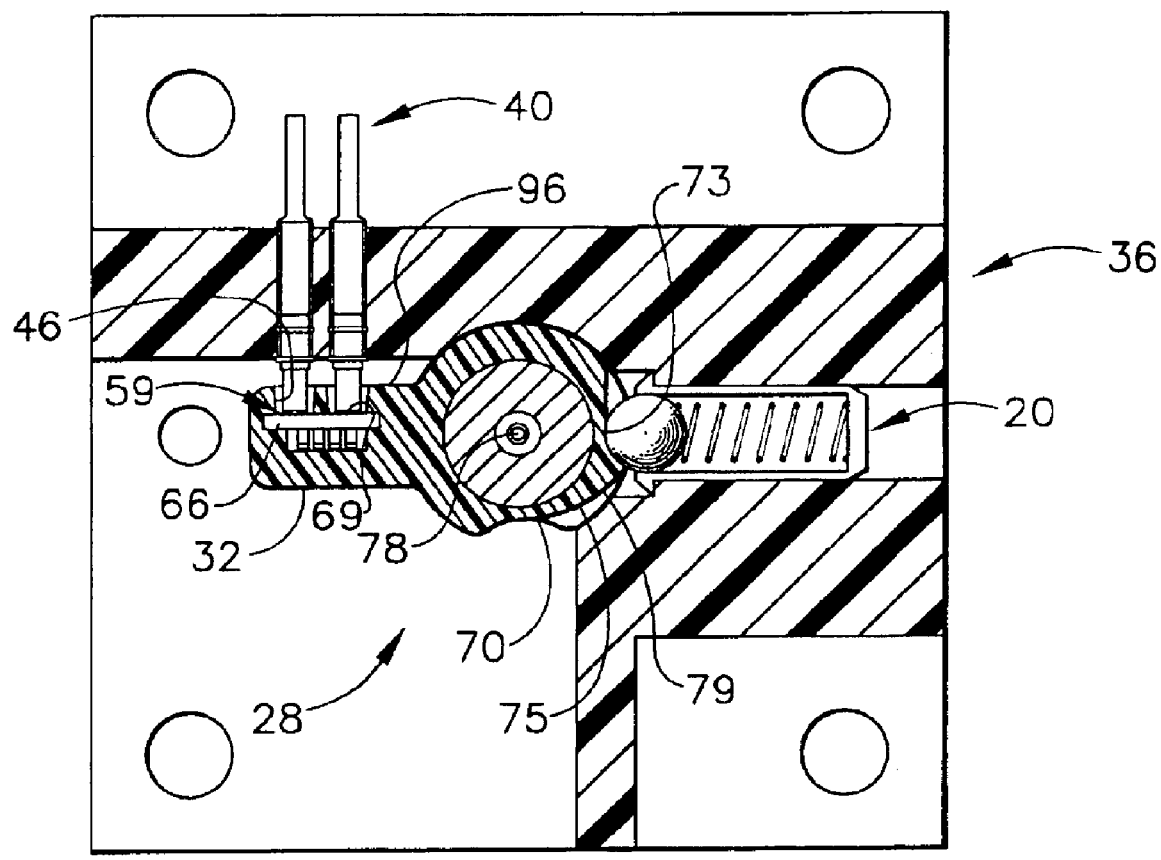
FIG. 14 is a section view taken generally along line 14—14 of FIG. 13.

FIGS. 13 and 14 depict connector 28 in the locked position. The user rotates connector 28 around longitudinal axis 78 until contact pads 59 are engaged with spring-loaded pins 40. Contact pads 59 approach and contact spring-loaded pins 40 in a direction substantially perpendicular to contact surfaces 69 of contact pads 59. The substantially perpendicular connection saves wear on spring-loaded pins 40 by minimizing sliding contact between the contact pads 59 and spring-loaded pins 40.

FIG. 14 shows spring-loaded pins 40 slightly depressed and contacting contact pads 59 on printed circuit board 66. Springs within spring-loaded pins 40 apply a force to printed circuit board 66 to maintain physical and electrical contact between spring-loaded pins 40 and contact pads 59 of printed circuit board 66. The applied force, transmitted to flange 32, tends to rotate connector 28 away from spring-loaded pins 40. When connector 28 is in the locked position, detent groove 70 contacts detent 20 at detent contact point 73. Detent 20, positioned within a deep portion of detent groove 70, applies a counteracting torque to prevent connector 28 from rotating flange 32 away from spring-loaded pins 40. Additional torque must be applied by the user to overcome the torque applied by detent 20 to rotate connector 28 away from the locked position.

Figure 15:
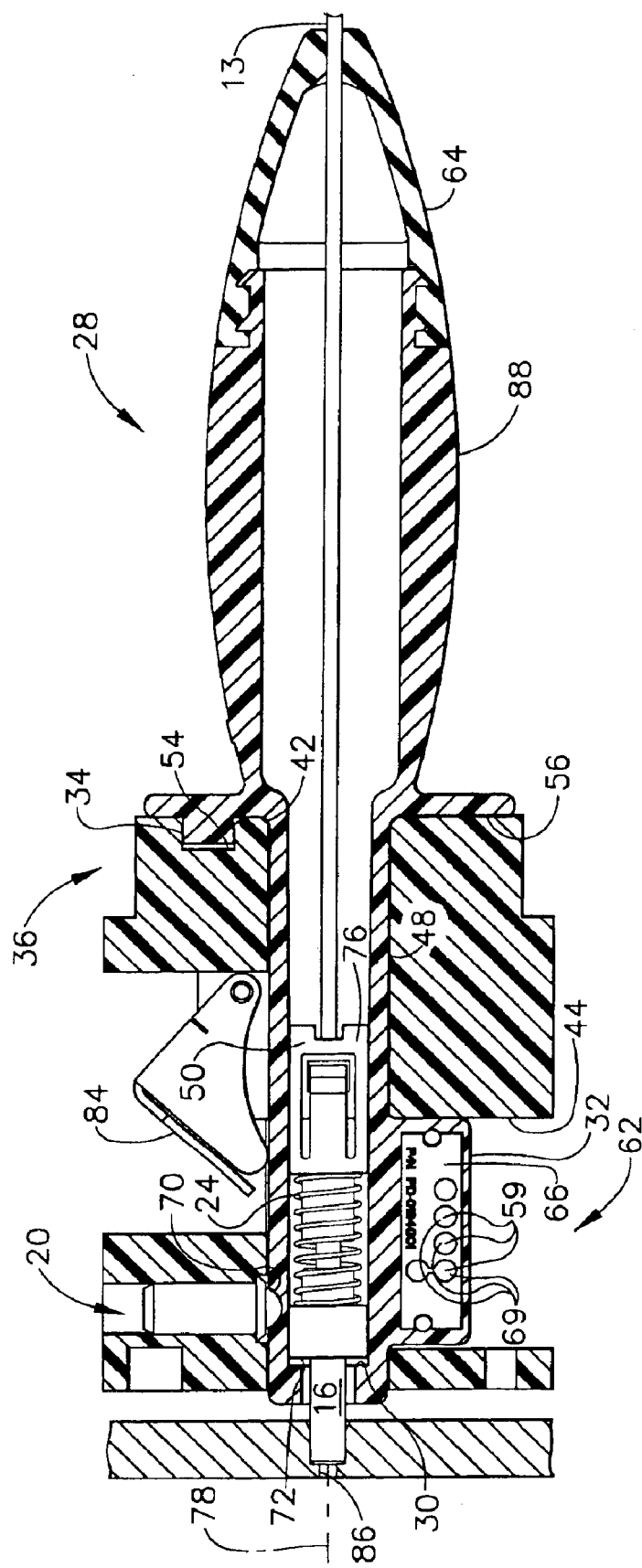
FIG. 15 is a section view taken along line 15—15 of FIG. 13.

FIG. 15 is a section view of connector 28 inserted into connector housing 36 and rotated to the locked position. In the locked position, connector 28 cannot be removed from connector housing 36 without rotation. The design of wall 44 to block flange 32 from proximal movement causes robust locking of the assembly. As connector 28 rotates from the unlocked position to the locked position, flange 32 rotates into a position distal to wall 44 and aligned with wall 44. The force generated by spring 24 reacts through spring retainer 26 through to connector 28 moving flange 32 against wall 44 while wall 44 obstructs flange 44 from moving proximally out of connector housing 36. The obstruction of flange 32 by wall 44 prevents accidental removal of connector 28. The accidental removal prevented would include removal caused by spring 24 overriding the restraint of detent 20 or by the user inadvertently pulling on connector 28 from handle portion 88 or from optical fiber 13.

When connector 28 is in the locked position, anti-torque feature 34 serves to keep the user from applying inadvertent stress on flange 32 and associated memory device 58. Continued rotation of connector 28 past the locked position causes anti-torque feature 34 to contact the end of slot 54 taking the stress caused by the applied torque.

With connector 28 in the locked position, memory device 58 can communicate electrically with main processor 25 on controller board 38 through contact pads 59, spring-loaded pins 40, and conductor cable 52. Information within memory device 58 may now be accessed by main processor 25. The information contained with memory device 58 may include calibration parameters, identification number, expiration date, and prior usage history of optical fiber assembly 12. Main processor 25 may use the information contained within memory device 58 to modify the energy output of laser 22. Also, main processor 25 may make decisions regarding the information contained within memory device 58. For example, main processor 25 may modify the energy delivered by laser 22 based on calibration parameters. As a further example, main processor 25 may generate an error message and display it on a display device on laser 22 if optical fiber assembly 12 is used at a time later than an expiration date recorded within memory device 58. As another further example, main processor 25 may prohibit use of optical fiber assembly 12 if a preset number of usages of optical fiber assembly 12 has been exceeded, or if a preset value for total energy transferred through optical fiber assembly 12 has been exceeded. Main processor 25 may write information to memory device 58 to be carried with optical fiber assembly 12. For example, main processor 25 may write to memory device 58 information concerning the type of treatment, date and time of use of optical fiber assembly 12, any errors generated, total number of uses for optical fiber assembly 12, or total energy transmitted through optical fiber assembly 12.

System 10, with optical fiber assembly 12 connected, may be used, for example, to apply laser light energy to tissue for therapeutic treatment of the tissue. The light energy may be used for treatment of diseases such as benign prostatic hypertrophy. After applying energy to tissue, the user removes connector 28 from connector housing 36. To remove connector 28 the user simply rotates connector 28 from the locked position to the unlocked position. After rotating connector 28, the user pulls on handle portion 88 easily removing connector 28.

It can be seen by those skilled in the art that embodiments other than those illustrated can make use of the present invention. Laser 22 could be any energy generator for many types of energy such as, for example, radio frequency energy, microwave energy, or ultrasound energy. Optical fiber assembly 12 could be an energy delivery device capable of delivering from the energy generator many types of useful energy. Spring-loaded pins 40 may be any conductive contacts such as, for example, electrical contact pin connectors, radio frequency link, optical link, magnetic link, or other link capable of information transfer. Contact pads 59 may be, for example, capable of transferring information by electrical, radio frequency, optical, or other means.

It will be recognized that equivalent structures may be substituted for the structures illustrated and described herein and that the described embodiment of the invention is not the only structure which may be employed to implement the claimed invention. As an example of an equivalent structure that may be used to implement the present invention, the flange 32 may have its thickness increased so one side becomes tangent to the barrel 48 to strengthen the flange 32. As a further example of an equivalent structure that may be used to implement the present invention, the anti-torque feature 34 may take the form of a circumferentially raised boss fitting into the slot 54 instead of the boss shown. As a further equivalent structure, the positions of spring loaded pins 40 and contact pads 59 may be reversed, placing spring loaded pins 40 on connector 28 and contact pads 59 on connector housing 36.

Figure 16:
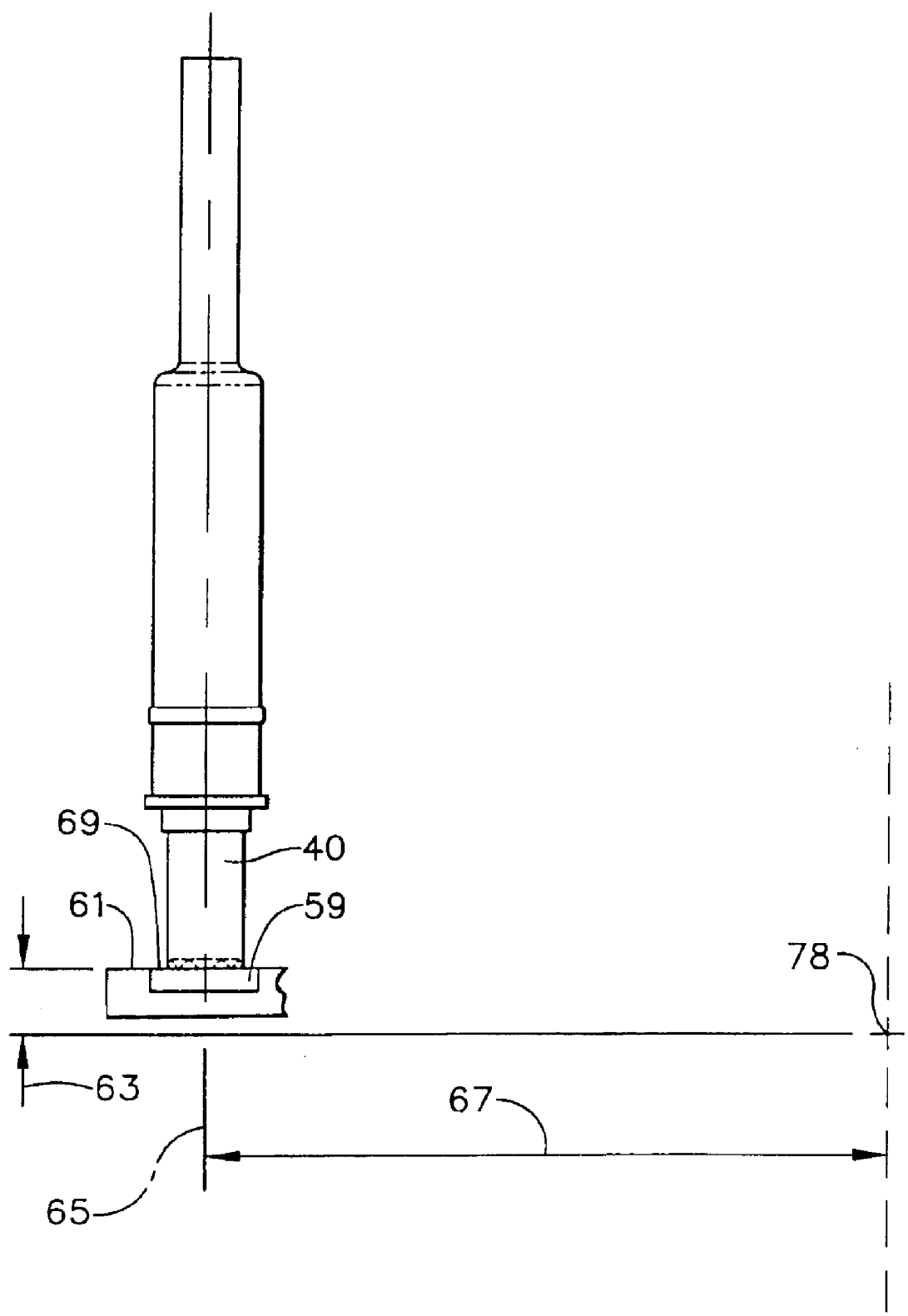
FIG. 16 is a schematic view showing substantially perpendicular engagement of a contact pad with a spring-loaded pin according to an embodiment of the present invention.

As an example of a further equivalent structure, FIG. 16 shows schematically that a contact pad 59 may be located on any surface of connector 28 that facilitates substantially perpendicular engagement of contact surface 69 of contact pad 59 with spring loaded pins 40 upon rotation of connector 28. For example, contact surface 69 may be located on any contact pad plane 61 of connector 28 passing parallel to longitudinal axis 78 at a first distance 63 from longitudinal axis 78. FIG. 16 further depicts contact pad perpendicular line 65 passing through contact pad 59 and perpendicular to contact surface 69. Contact pad perpendicular line 65 also does not intersect longitudinal axis 78, and is thus skew to longitudinal axis 78. If contact surface 69 of contact pad 59 lies in a plane passing parallel to longitudinal axis 78 and contact pad perpendicular line 65 is skew to longitudinal axis 78, a position for spring loaded pins 40 may be found for substantially perpendicular engagement with contact surface 69. In a limiting case, first distance 63 may be zero, so that contact surface 69 lies directly in the plane of longitudinal axis 78.

FIG. 16 further illustrates contact pad 59 offset by a second distance 67 from longitudinal axis 78. The larger second distance 67 becomes, the more closely the arc traveled by a contact pad 59 as connector 28 is rotated approximates a straight line. It has been found that a second distance 67 of at least about 0.3 inches adequately approximates straight-line engagement of contact pad 59 with its mating spring loaded pin 40.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A connector for attaching an energy delivery device to an energy generator by rotation of said connector about a longitudinal axis, said connector comprising:
   a handle portion;
   an energy transfer attachment for transferring energy from said energy generator to said energy delivery device, said energy transfer attachment extending from said handle portion;
   a contact pad plane defined on said connector, said contact pad plane parallel to said longitudinal axis; and
   at least one contact pad having a contact surface, said contact surface located on said contact pad plane, wherein a line through said contact surface and perpendicular to said contact pad plane is skew to said longitudinal axis;
   wherein the connector comprises a barrel longitudinally extending from said handle, and said contact pad is located within a flange radially extending from said barrel; and wherein said contact pad is accessible through at least one access opening located on said flange.

2. The connector of claim 1 further comprising a memory device attached to said connector, said memory device in electrical communication with said contact pad.

3. The connector of claim 2 wherein said contact pad and said memory device are located on a printed circuit board insert molded within said flange.

4. A connector for attaching an energy delivery device to an energy generator by rotation of said connector about a longitudinal axis, said connector comprising:
   a handle portion;
   a barrel extending longitudinally from said handle portion;
   an energy transfer attachment for transferring energy from said energy generator to said energy delivery device, said energy transfer attachment located on said barrel;
   a flange radially extending from said barrel; and
   at least one contact pad located on said flange;
   wherein said at least one contact pad is accessible through an access opening located on said flange.

5. The connector of claim 4 further comprising a memory device attached to said connector, said memory device in electrical communication with said contact pad.

6. The connector of claim 5 wherein said contact pad and said memory device are located on a printed circuit board insert molded within said flange.

7. A system for transferring energy to tissue, said system comprising:
   an energy generator including a connector housing;
   at least one conductive contact affixed to said connector housing;
   an energy delivery device having a connection end;

a connector mounted on said energy delivery device at said connection end, said connector having a longitudinal axis, and said connector removably attachable to said housing and rotatable about said longitudinal axis relative to said housing between an unlocked position and a locked position;

a flange radially extending from said connector; and at least one contact pad located on said flange, said contact pad having a contact surface, wherein rotation of said connector about said longitudinal axis from said unlocked position to said locked position engages said contact pad to said conductive contact in a direction substantially perpendicular to said contact surface.

8. The system of claim 7 wherein said contact pad is located on a printed circuit board, said printed circuit board is insert molded within said flange, and said flange contains at least one pad access opening adjacent said contact pad.

9. The system of claim 7 wherein said system further comprises a wall affixed to said connector housing and wherein in said unlocked position said flange clears said wall to allow removal of said connector from said housing and in said locked position said flange is obstructed by said wall to prevent removal of said connector from said housing.

10. The system of claim 9 further comprising a detent mounted on said housing, said detent engaging said connector when said connector is connected to said housing.

11. The system of claim 10 further comprising:

an anti-torque feature mounted on said connector; and a receiving feature mounted an said housing, said receiving feature mating with said anti-torque feature upon assembly of said connector with said housing.

12. The system of claim 7 further comprising:

a computer positioned within said energy generator, said computer in electrical communication with said conductive contact; and a memory device positioned on said connector, said memory device in electrical communication with said contact pad, wherein said engagement of said contact pad to said conductive contact places said memory device in electrical communication with said computer.

13. A system for treatment of tissue using light energy, said system comprising:

a laser having an associated computer and a connector housing;

at least one conductive contact within said connector housing;

an optical fiber assembly having a connection end;

a connector located at said connection end, said connector rotatably attachable to said connector housing, and said connector capable of transferring light energy from said laser to said optical fiber assembly;

a flange extending from said connector; and at least one contact pad, said contact pad having a contact surface and said contact pad located within said flange wherein rotation of said connector engages said contact pad with said conductive contact in a direction substantially perpendicular to said contact surface.

14. The system of claim 13 wherein said connector further comprises an attached memory device, said memory device in electrical communication with said contact pad.

15. The system of claim 14 wherein said memory device and said contact pad are located on a printed circuit board insert-molded within said flange.

16. The system of claim 15 wherein said system further comprises a wall affixed to said connector housing and wherein said wall obstructs said flange to prevent removal of said connector from said connector housing when said contact pad is engaged to said conductive contact.

17. The system of claim 16 wherein said conductive contact comprises a spring-loaded pin.

18. The system of claim 17 wherein engaging said contact pad to said spring-loaded pin electrically connects said memory device to said computer for the exchange of information.

19. A method of treating tissue with light energy, said method comprising:

providing a laser having an associated computer providing a connector housing, said connector housing having at least one conductive contact and said connector housing attached to said laser;

providing an optical fiber assembly, said optical fiber assembly having a connector attached at one end and said connector having at least one contact pad located thereon, said contact pad having a contact surface;

providing a memory device located on said optical fiber assembly;

inserting said connector into said housing;

rotating said connector within said housing to engage said contact pad with said conductive contact in a direction substantially perpendicular to the contact surface;

exchanging information between said memory device and said computer;

transferring light energy through said connector to said optical fiber assembly; and treating tissue with said light energy.

* * * * *